United States Patent [19]

Trouet et al.

[11] 4,376,765

[45] Mar. 15, 1983

[54] MEDICAMENTS, THEIR PREPARATION AND COMPOSITIONS CONTAINING SAME

[75] Inventors: Andre B. L. Trouet, Winksele; Michele M. L. G. Masquelier, Brussels; Roger M. Baurain, Wezembeek, all of Belgium

[73] Assignee: Institut International de Pathologie Cellulaire et Moleculaire, Brussels, Belgium

[21] Appl. No.: 249,487

[22] Filed: Mar. 31, 1981

[30] Foreign Application Priority Data

Mar. 31, 1980 [BE] Belgium ............................ 882541

[51] Int. Cl.³ ..................... A61K 37/00; C07C 103/52
[52] U.S. Cl. .............................. 424/177; 260/112.5 R
[58] Field of Search ................ 260/112.5 R; 424/177

[56] References Cited

U.S. PATENT DOCUMENTS

| | | | |
|---|---|---|---|
| 4,161,519 | 7/1979 | Talwar | 424/177 |
| 4,201,770 | 5/1980 | Stevens | 260/112.5 R |
| 4,256,632 | 3/1981 | Levin et al. | 260/112.5 R |
| 4,272,433 | 6/1981 | Nishino | 260/112.5 R |

*Primary Examiner*—Delbert R. Phillips

[57] ABSTRACT

The invention relates to a new pharmaceutical form of a medicament of the formula Carrier-Spacer arm-Drug in which
"Drug" represents an active principle provided with a free amino function
"Spacer arm" represents a peptidic chain of the X-L-Leu type and
"Carrier" is a proteinic macromolecule adapted to the drug.

13 Claims, No Drawings

MEDICAMENTS, THEIR PREPARATION AND COMPOSITIONS CONTAINING SAME

The present invention relates to new pharmaceutical forms of an active principle, the preparation thereof and compositions containing such products.

A medicament or a drug, in order to exert its effect, should penetrate into the appropriate cell called target cell. Generally such penetration takes place by diffusion of the medicament or the drug through the cellular wall. Under these conditions, an equilibrium is reached between the concentration of the active principle in the cell and the concentration in the external medium. On the other hand, the medicament does not always penetrate selectively into the target cells to be acted upon, and by its action on the healthy cells, the medicament may exert bad secondary effects which may adversely affect the utility thereof.

Another model of intracellular penetration is based on an endocytic mechanism in which the macromolecules are included in vacuoles formed by invagination of the cellular membrane before fusing with the lysosomes.

This endocytic mechanism whose preeminency depends upon the cellular type, may be used in therapeutics to increase the selectivity of therapeutical agents towards cells susceptible to said mechanism.

In order that the therapeutical agent may have a sufficient size to take part to said endocytic mechanisms, it is possible to bind the active principle to a macro-molecule such as a protein which will be designated as "carrier". In order that the medicament may exert its effects wholly or partly, it is necessary that it be released from the interior or in the immediate vicinity of the target cell. In other words, the active principle-carrier or drug-carrier conjugate should meet the following three criteria:

(1) be stable in the blood circulation before reaching the target cells
(2) be dissociated or cleaved in the target cells or in the immediate vicinity thereof,
(3) be able to regenerate the drug in its active form.

In order to meet the first of these criteria, it is necessary that the bond between the drug and the carrier be of covalent nature and that such covalent bond resists the hydrolases which are present in the serum.

The drug-carrier conjugate penetrating into the target cells by an essentially endocytic mechanism, it is necessary to take into account the properties of the lysosomes in order to meet the second criterion. As a matter of fact, the bond between the drug and the carrier may be split either chemically in acid medium or enzymatically by means of the acid hydrolases of the lysosomes. It is however necessary taking into account the third criterion, that the drug be released in its active form. It has been found that such a result cannot be obtained if the active principle is directly bound to the macromolecule.

It has been found according to the present invention, that a medicament having the desired properties can be obtained by inserting a temporary bond called "spacer arm" between the drug and the carrier.

The present invention concerns new pharmaceutical forms of an active principle which may schematically be represented by the formula Carrier-Spacer arm-Drug (I)

the process for preparing them and compositions containing them.

According to the invention, the drug consists of an active principle which acts intracellularly and which contains in its molecule a free amino function. Examples of drugs having a free amino function are anthracyclines with an antitumoral activity such as daunorubicine or doxorubicine, or quinoleines having antimalarial and antileishmanial properties, such as primaquine.

According to the invention, the arm is of peptidic nature and contains preferably 3 or 4 aminoacids. It is particularly important that the aminoacid being bound to the free amino function of the drug through its carboxylic function, has an asymmetric carbon atom and has the L-configuration because the peptidases or the lysosomal hydrolases only cut the peptidic bonds in the alpha position with respect to an asymmetric carbon. The aminoacid composing the peptidic spacer arm could be selected among the following L-aminoacids: α-aminobutyric acid, γ-aminobutyric acid, ε-aminocaproic acid, arginine, asparagine, aspartic acid, cysteic acid, cysteine, glutamine, glutamic acid, glycine, histidine, 4-hydroxyproline, isoleucine, leucine, lysine, methionine, norleucine, norvaline, phenylalanine, proline, serine, threonine, tryptophane, tyrosine and valine. Of particular interest to play this function is L-leucine. For example, among the derivatives of the amino function of the antitumoral anthracyclines, such as daunorubicine, it has been shown that N-L-leucyl-daunorubicine is the product which, under the conditions of lysosomal digestion, releases the most important amount of daunorubicine. Thus after two hours hydrolysis at pH 4.5, N-L-leucyl-daunorubicine releases 65% of free daunorubicine and 90% at pH 6.0. Other interesting aminoacids include L-tyrosine and L-isoleucine since, when linked to daunorubicine, they regenerate at pH 6.0 respectively 70 and 60% of daunorubicine by the action of lysosomal peptidase. However L-leucine has been selected as the aminoacid adjacent to the drug or active principle since N-L-leucyl-daunorubicine, N-L-leucyl-doxorubicine and N-L-leucyl-primaquine are stable in the serum and regenerate rapidly the free drug or active principle when submitted to the lysosomal digestion.

If the arm between daunorubicine and carrier is a L-leucine, after 24 hours hydrolysis at pH 6.0 of the product carrier-spacer arm-drug by purified lysosomal enzymes, 15% of the drug will be released in the form of free daunorubicine. In addition, a much higher rate of release of the free drug is obtained when the number of aminoacids making up the peptidic arm increases and may be as high as 78% when the intermediate peptide is made of a sequence of 4 aminoacids. Thus according to the invention, the intermediate "spacer arm" preferably is represented by the sequence X—L—Leu in which L-Leu is bound through its carboxylic function to the amino function of the drug and X represents 1, 2 or 3 aminoacids, which may be identical or different and are selected from L-alanine, glycine and L-leucine.

Of particular interest are the peptidic "spacer arm" L-ala-L-leu, L-leu-L-ala-L-leu, L-ala-L-leu-L-ala-L-leu, (L-ala)$_3$-L-leu, L-ala-L-leu-gly-L-leu, (gly-L-leu)$_2$;

among them, the sequences in which L-ala and L-leu alternate with one another, are particularly suitable.

According to the invention, the "carrier" is a macromolecule which can be selectively endocytosed by the target cells. Preferably the macromolecule is a protein the peptidic nature of which is related to the action aimed at for the "drug". For example, with derivatives of antitumoral anthracyclines, advantageously bovine serum albumine (BSA), fetuine, immunoglobulin or peptidic hormones, such as lactotropine or lactogenous placentary hormone may be used. With antimalarial quinoleines, it is particularly interesting to use asialofetuine or any other glycoprotein carrying terminal galactosyl residues or moieties which shall be captured specifically by the hepatocytes where the parasites are found.

With antileishmanial quinoleines, it is particularly suitable to use glycoproteins carrying terminal mannosyl moieties which shall be captured specifically by the macrophages where the parasites are located.

According to the invention, the new pharmaceutical forms may be obtained by reacting a product of the general formula $$X-L-leu-Drug \qquad (II)$$

wherein the term "Drug" and the symbol "X" are defined as previously, with a protein under the conditions normally used for creating a peptidic bond between the free amino function of the terminal aminoacid of the product of general formula II and the free acid functions of the protein.

Generally the reaction is effected in a suitable buffered medium such as phosphate buffered saline (PBS) in the presence of a condensation agent such as a carbodiimide as 1-ethyl-3-(3-dimethylaminopropyl)-carbodiimide at a temperature between 0° and 30° C. It is particularly advantageous to perform the reaction in the absence of light.

The new pharmaceutical form according to the invention is separated from the reaction mixture using the physical or physicochemical methods such as chromatography on a suitable support.

The "spacer arm" also can be attached to the free amino functions of the protein after succinylation of the free amino function of the terminal aminoacid of the product of general formula II and activation of the terminal carboxylic function of the succinyl by N-hydroxysuccinimide. The condensation of the drug-carrying arm with the carrier then takes place in the absence of a condensation agent to give the new pharmaceutical forms of general formula I.

In accordance with the invention, the new pharmaceutical forms of general formula I in which the peptidic "spacer arm" is bound to the "carrier" through a succinyl moiety also may be obtained by action of a product of general formula II on the succinylated protein.

It is particularly advantageous to act in the presence of a condensation agent such as a carbodiimide, more particularly 1-ethyl-3-(3-dimethylaminopropyl)-carbodiimide at a temperature between 0° and 30° C. and preferably in the absence of light.

The product of general formula II can be obtained by condensation of an appropriate aminoacid or a peptide in the acid form, the amino functions of which are protected, with a drug carrying a free amino function or derivative of said drug which carries a free amino function in the presence of a condensation agent in accordance with the conventional methods used in peptidic chemistry.

Preferably one effects first condensation of L-leucine the amino function of which is protected, with the "drug", followed by condensation of the aminoacids intended to make up the spacer arm on the N-L-leucyl-"Drug".

As condensation agent, there is used more particularly a carbodiimide in an organic solvent such as dimethylformamide, methylene chloride or acetonitrile. The acid function of the aminoacid also may be activated in the ester form with N-hydroxysuccinimide or in the mixed anhydride form.

The amino protecting groups are groups such as acyl (formyl) or urethane (fluorenylmethoxycarbonyl, benzyloxycarbonyl, tertio-butyloxycarbonyl) or arylalkyl (trityl). These groups also thereafter may be removed under conditions which do not destroy the peptidic bond formed. For example, when the amino function is protected by a trityl radical, said protecting group can be removed by hydrolysis in acid medium.

The new pharmaceutical forms of the invention are particularly useful to permit a selective action in the activity area of the base drug. The action of the new medicaments being more specific, the same effect is obtained with smaller amounts of drug; in addition, it is possible to attenuate strongly the secondary adverse effects thanks to less dissemination of the drug outside the target cells.

The new products of the invention show particularly valuable properties.

Thus the products in which the drug is daunorubicine inhibit in vitro the growth of cancerous cells such as cells of L 1210 leukemia in an appropriate medium. For example, after 72 hours of culture, BSA-succinyl-L-Ala-L-Leu-L-Ala-L-Leu-Daunorubicine at a concentration near 10 $\mu g/cm^3$, causes 90% of inhibition of the growth of L 1210 leukemia cells.

In mice inoculated intraperitoneally with L 1210 leukemia and treated by intraperitoneal route, the fetuine-succinyl-L-Ala-L-Leu-L-Ala-L-Leu-daunorubicine and the BSA-succinyl-L-Ala-L-Leu-L-Ala-L-Leu-daunorubicine show at equal doses expressed as daunorubicine a markedly better activity than that of daunorubicine or L-leucyl-daunorubicine, together with less toxicity.

For example, at a dose of 5 mg/kg expressed as daunorubicine, fetuine-L-Ala-L-Leu-L-Ala-L-Leu-daunorubicine provides an increase of life span (ILS) close to 194% with 8 surviving mice of 10 after 30 days of observation, whereas under the same conditions, daunorubicine being already toxic at that dose, causes a ILS of about 7%.

The products of the invention in which the drug is primaquine when administered intravenously at doses between 10 and 30 mg/kg before infestation by Plasmodium berghei, provide an increase of life span higher than 400% when compared to the untreated control animals.

The following examples are given for non restrictive purposes and show how to put the invention into practice.

EXAMPLE 1

(a) Preparation of L-alanyl-L-leucyl-L-alanyl-L-leucyl-daunorubicine

To an ice cold solution of 1 g of daunorubicine (1.77 mmoles) in 200 cm$^3$ of borate buffer at pH 10.2, being stirred under nitrogen, one adds a solution of 320 mg of N-carboxyanhydride of L-leucine (2.04 mmoles) in 10 cm$^3$ of acetone at $-10°$ C. After 5 minutes of stirring, the pH is brought to 3.5 by adding 6 N sulfuric acid and then, after 15 minutes, the reaction mixture is neutralized with 1 N sodium hydroxide. The solution is extracted with 150 cm$^3$ of methylene chloride. The organic phase is dried over sodium sulfate. After filtration and concentration to dryness under reduced pressure (20 mm of Hg) at a temperature below 50° C., the product is purified by chromatography on 60 g of silica by eluating with a mixture of chloroform and methanol (95-5 by volumes). In that way, one obtains after evaporation of the solvent 690 mg of N-L-leucyl-daunorubicine which by addition of the theoretical amount of hydrochloric acid provides 715 mg of hydrochloride of L-leucyl-daunorubicine melting at 201° C. with decomposition.

To a stirred solution of 677 mg of L-leucyl-daunorubicine (1 mmole) in 16 cm$^3$ of dimethylformamide, one adds 498 mg of N-trityl-L-alaninate of N-hydroxysuccinimide (2.12 mmoles) and 0.140 cm$^3$ of triethylamine. The reaction mixture is stirred for 24 hours at a temperature of about 20° C. After evaporation of the solvent, the residue is dissolved in 10 cm$^3$ of a mixture of chloroform and methanol (99-1 by volumes), and then filtered in a column of 45 g of silicagel. After evaporation of the solvent, one obtains 450 mg of N-trityl-L-alanyl-L-leucyl-daunorubicine. This product is treated cold with a 75% solution of acetic acid, then the solution is neutralized by adding 12 N ammonia. After extraction with chloroform, drying on sodium sulfate, filtration and evaporation of the solvent, hydrochloride formation and filtration of triphenylcarbinol, one obtains 470 mg of hydrochloride of L-alanyl-L-leucyl-daunorubicine melting at 205° C. with decomposition.

One dissolves 250 mg of the hydrochloride of L-alanyl-L-leucyl-daunorubicine into 6 cm$^3$ of dimethylformamide followed by addition of 0.046 cm$^3$ of triethylamine and 166 mg of N-trityl-L-leucinate of N-hydroxysuccinimide. By acting as described previously for the preparation of L-alanyl-L-leucyl-daunorubicine, one obtains 130 mg of hydrochloride of L-leucyl-L-alanyl-L-leucyl-daunorubicine, melting at 170° C. with decomposition.

One dissolves 98 mg of hydrochloride of L-leucyl-L-alanyl-L-leucyl-daunorubicine in 5 cm$^3$ of dimethylformamide. One adds 0.016 cm$^3$ of triethylamine and 57 mg of N-trityl-L-alaninate of N-hydroxysuccinimide. By acting as previously described for the preparation of L-alanyl-L-leucyl-daunorubicine, one obtains 65.5 mg of hydrochloride of L-alanyl-L-leucyl-L-alanyl-L-leucyl-daunorubicine melting at 217° C. with decomposition.

(b) Coupling with bovine serum albumin

To 8 mg of hydrochloride of L-alanyl-L-leucyl-L-alanyl-L-leucyl-daunorubicine dissolved in 2 cm$^3$ of distilled water, one adds 100 mg of bovine serum albumin dissolved in 3 cm$^3$ of phosphate buffer (Phosphate Buffered Saline, PBS).

The mixture is left for 15 hours in the dark at a temperature of about 20° C. then the solution is filtered in a column of 150 cm$^3$ of Biogel P-100 by eluating with phosphate buffer (Phosphate Buffered Saline or PBS).

The first fraction (14 cm$^3$) which corresponds to the coupled product is filtered in a column containing 1 g of Porapak Q (Waters) so as to remove possible traces of drug fixed in a non-covalent way. The solution is sterilized by filtration with a 0.2$\mu$ Millipore filter and kept at $-20°$ C.

One thus obtains a solution containing 50 $\mu$g of drug per cm$^3$ and 3 mg of bovine serum albumin per cm$^3$.

EXAMPLE 2

(a) Succinylation of N-L-alanyl-L-leucyl-L-alanyl-L-leucyl-daunorubicine.

One dissolves 130 mg of hydrochloride of N-L-alanyl-L-leucyl-L-alanyl-L-leucyl-daunorubicine (0.130 mmole) in 15 cm$^3$ of twice- or bidistilled water.

One adds 2 times 14 mg of succinic anhydride (2 times 0.14 mmole) in small batches while maintaining the pH at 7.5 by adding 1 N sodium hydroxide.

Upon completion of the reaction, the pH of the reaction mixture is adjusted to 5.5, the product formed is extracted with 3 times 20 cm$^3$ of chloroform. The organic phase is washed carefully 3 times with bidistilled water, and then dried on sodium sulfate.

After evaporation of the organic phase, there is obtained 100 mg of red powder (yield 72%) which is put into suspension in 20 cm$^3$ of water. One adds 1 cm$^3$ of a 0.1 N solution of sodium hydroxide. The solution thus obtained is lyophilised or freeze dried. This provides 103 mg of the sodium salt of succinyl-L-ala-L-leu-L-ala-L-leu-daunorubicine.

(b) Coupling with bovine serum albumin

One dissolves 8.7 mg of succinyl-alanyl-leucyl-alanyl-leucyl-daunorubicine into 2 ml of bidistilled water and one adds 100 mg of bovine serum albumin dissolved in 2 ml of PBS and 10 mg of soluble carbodiimide [1-ethyl-3-(3-dimethylaminopropyl)-carbodiimide, Pierce Chem., U.S.A.] dissolved in 1 ml of PBS. The mixture is stirred slowly at 4° C. for 16 hours in darkness and the coupled drug is separated from the free drug by molecular sieving using a column of Biogel P-100 (Biorad Laboratories, USA). The first peak of elution contains 12.6 $\mu$g drug/ml and is collected in a volume of 46 ml. This provides a yield of coupling of 16.9% and a molar ratio drug/protein of 1.4. The solution is filtered on 0.2$\mu$ Millipore and kept at 4° C.

EXAMPLE 3

1. Preparation of succinylated fetuine.

One dissolves 1 g of fetuine (type III, Sigma Chem., USA) in which 1 g of fetuine corresponds to 0.33 mmole of free amine, into 10 cm$^3$ of twice-distilled water. The pH is adjusted to 7.5 by adding 0.5 N sodium hydroxide. To that solution, one adds 68 mg of succinic anhydride (0.68$\mu$ mole) in small batches while maintaining the pH at about 7.5 by means of 1 N sodium hydroxide. One adds again 68 mg of succinic anhydride and then dialyzes the solution against 3 times 2 liters of twice-distilled water at 4° C.

2. Coupling with L-alanyl-L-leucyl-L-alanyl-L-leucyl-daunorubicine.

One dissolves 9.6 mg (10.3$\mu$ moles) of hydrochloride of L-alanyl-L-leucyl-L-alanyl-L-leucyl-daunorubicine into 2.5 cm$^3$ of water. Thereafter one adds 2.5 cm$^3$ of a solution of succinylated fetuine at 20 mg/cm$^3$ (1.04 $\mu$ mole). Thereafter one adds 3 mg (15.6$\mu$ moles) of 1-ethyl-3-(3-diethylaminopropyl)-carbodiimide. The reaction mixture is left in darkness for 6 hours at 4° C. One then adds 1.5 mg of 1-ethyl-3-(3-diethylaminopropyl)-carbodiimide and leaves the reaction mixture for 15 hours at about 20° C.

The solution is then filtered using a column of Biogel P-100 for separating the free drug from the coupled drug. One thus obtains a yield of coupling of 83% and a molar ratio drug/protein of about 7.

EXAMPLE 4

1. Preparation of L-leucyl-L-alanyl-L-leucyl-doxorubicine.

(a) A mixture of 120 mg of hydrochloride of L-leucyl-doxorubicine (the preparation properties and use of which are described in Belgian Pat. No. 869,485 and corresponding U.S. Pat. application No. 055,291 filed on July 5, 1979 in the name of Roger M. Baurain and Andre B. Trouet and the contents of which are incorporated herein by reference) and 80 mg of N-trityl-L-alaninate of N-hydroxysuccinimide in 4 cm³ of dimethylformamide is stirred for 24 hours in the presence of 0.024 cm³ of triethylamine. The evolution of the reaction is followed by thin layer chromatography (T.L.C.). When the reaction is completed, the solvent is evaporated under reduced pressure. The residue obtained is purified by column chromatography using 10 g of silicagel by eluating mixtures of chloroform and methanol which progressively contain from 1 to 10% of methanol.

The eluate is recovered in a plurality of fractions and those containing N-trityl-L-alanyl-L-leucyl-doxorubicine are collected.

Removal of the protecting group of the amino function of the alanine is effected at room temperature by means of 75% acetic acid. After 20 minutes, the solution is cooled to 0° C., neutralized with concentrated NH₄OH. The solution is filtered. The precipitate is washed with distilled water and the filtrate is extracted with chloroform and dried on anhydrous Na₂SO₄. After evaporation of the solvent under reduced pressure, the hydrochloride of N-L-ala-L-leu-doxorubicine is obtained by addition of one equivalent of 1 N HCl.

(b) The N-L-leucyl-L-alanyl-L-leucyl-doxorubicine is obtained by following the method described in a, however starting from 120 mg of the hydrochloride of N-L-alanyl-L-leucyl-doxorubicine and 85 mg of N-trityl-L-leucinate of N-hydroxysuccinimide.

2. Preparation of N-succinyl-L-leucyl-L-alanyl-L-leucyl-doxorubicine.

Succinylation of N-L-leucyl-L-alanyl-L-leucyl-doxorubicine is effected as described in Example 2a for L-ala-L-leu-L-ala-L-leu-daunorubicine.

3. Coupling of N-succinyl-L-leucyl-L-alanyl-L-leucyl-doxorubicine with bovine serum albumin.

Coupling is effected as described in Example 2b for N-succinyl-L-alanyl-L-leucyl-L-alanyl-L-leucyl-daunorubicine.

EXAMPLE 5

1. Preparation of succinylated asialofetuine.

A solution of 1 g of fetuine (Sigma Chem., USA) in 10 cm³ of acetate buffer (0.2 M) at pH 5.5 is passed in closed circuit through a column of insolubilized neuraminidase (Sigma Chem., USA) maintained at 45° C. After 48 hours, the solution of asialofetuine is recovered; the gel obtained is washed with 2 M sodium chloride and the sialic acid is removed by dialysis of the solution for 12 hours against distilled water. The asialofetuine is purified by passing through a column of 125 cm³ of diethylaminoethyl cellulose (DEAE) which is eluated by a 0.01 M Tris buffer at pH 8. Fractions of 150 drops are collected by means of a Gilson fraction collector. The asialofetuine containing tubes are gathered and the solution thus obtained is dialyzed against water and then freeze dried.

2. Preparation of N-L-leucyl-primaquine.

(a) For 24 hours there is stirred a mixture of 600 mg of primaquine (2.321 mmoles) and 1.5 g of fluorenylmethoxycarbonyl-L-leucinate of N-hydroxysuccinimide (3.36 mmoles) in 15 cm³ of dimethylformamide. The evolution of the reaction is followed by thin layer chromatography. When the reaction is ended the solvent is evaporated under reduced pressure. The residue obtained is purified by chromatography on silicagel by eluating with mixtures of chloroform and methanol which progressively contain from 1 to 10% of methanol and finally with a mixture of chloroform, methanol and concentrated ammonia (900-100-8 by volumes). The eluate is recovered in a plurality of fractions which are examined with thin layer chromatography with respect to standards or controls after detection in the ultraviolet.

Elimination of the protecting group of the amino function of L-leucine is effected by means of piperidine. The precipitate obtained is separated by filtration and the filtrate is neutralized at pH 7 with a 1 N hydrochloric acid solution. The L-leucyl-primaquine is extracted with chloroform (200 cm³). The organic phase is dried over sodium sulfate. After filtration and concentration under reduced pressure (20 mm of mercury), one obtains 647 mg of L-leucyl-primaquine. To said 647 mg of L-leucyl-primaquine (174 mmoles), one adds 3.48 cm³ of 1 N hydrochloric acid. A solution of L-leucyl-primaquine dihydrochloride is thus obtained.

The N-L-leucyl-primaquine also may be prepared in the following way.

(b) To a solution of 7.68 g of primaquine (0.030 mole) in 125 cm³ of dry chloroform cooled to 0° C., one adds dropwise 4.65 g of N-carboxyanhydride of L-leucine (0.030 mole) in 50 cm³ of dry ether. The reaction is completed in 30 minutes. After evaporation of the solvent, the product is purified by chromatography. 6.7 g of L-leucyl-primaquine are thus obtained.

3. Preparation of L-alanyl-L-leucyl-primaquine.

A mixture of 4 g of L-leucyl-primaquine (10.75 mmoles) and 4.65 g of trityl L-alaninate of N-hydroxysuccinimide in 30 cm³ of dimethylformamide is stirred. The evolution of the reaction is followed by thin layer chromatography. After evaporation of the solvent under reduced pressure (20 mm of mercury), the product is purified by chromatography on silica by eluating with mixtures of chloroform and methanol which progressively contain from 1 to 10% of methanol.

One obtains in that way 5.21 g of N-trityl-L-alanyl-L-leucyl-primaquine which is treated with 50 cm³ of 75% acetic acid. The precipitate of triphenyl-carbinol is separated by filtration, the filtrate is neutralized cold by addition of concentrated ammonia (50 cm³) up to pH 7. After extraction of the reaction mixture with chloroform, the organic phase is dried over sodium sulfate.

After filtration and evaporation of the solvent under reduced pressure (20 mm of mercury), one obtains 3.45 g of L-alanyl-L-leucyl-primaquine. To 3.45 g of L-alanyl-L-leucyl-primaquine (7.78 mmoles) one adds 15.58 cm³ of a 1 N hydrochloric acid solution. There is thus obtained a solution of dihydrochloride of L-alanyl-L-leucyl-primaquine which is freeze dried.

4. Coupling of N-L-alanyl-L-leucyl-primaquine with succinylated asialofetuine.

332 mg of asialofetuine ($7.10^{-3}$ mmoles) are dissolved in 2.5 cm³ of phosphate buffer (Phosphate Buffered Saline) and 50 mg of dihydrochloride of L-alanyl-L-leucyl-primaquine and 50 mg of 1-ethyl-3-(3-dimethylaminopropyl)carbodiimide are added. These ingredients are left in contact with one another for 15 hours in darkness and at a temperature of about 20° C. The reaction mixture is filtered on a column of 125 cm³ of Biogel P-100. Fractions of 150 drops are collected.

Asialofetuine-L-alanyl-L-leucyl-primaquine is collected in fractions 6 to 12.

EXAMPLE 6

1. Preparation of N-L-leucyl-L-alanyl-L-leucyl-primaquine.

The synthesis of the tripeptidic derivative of primaquine is effected as described in Example 5§3 starting from N-L-alanyl-L-leucyl-primaquine obtained as described in Example 5§3, and N-trityl-L-leucinate of N-hydroxysuccinimide.

2. Preparation of N-L-alanyl-L-leucyl-L-alanyl-L-leucyl-primaquine.

This tetrapeptidic derivative of primaquine is prepared as described in Example 5§3 starting from N-L-leucyl-L-alanyl-L-leucyl-primaquine obtained as described in Example 6§1 and N-trityl-L-alaninate of N-hydroxysuccinimide. The dihydrochloride of N-L-alanyl-L-leucyl-L-alanyl-L-leucyl-primaquine has a Rf of 0.29 in the T.L.C. system of CHCl₃—MeOH— 26% NH₄OH (900:100:9; V/V) and a Rf of 0.34 in the system CHCl₃—MeOH—H₂O (120:20:1; V/V).

3. Coupling of N-L-alanyl-L-leucyl-L-alanyl-L-leucyl-primaquine with succinylated asialofetuine.

The coupling of the tetrapeptidic derivative of primaquine with succinylated asialofetuine is effected as described in Example 5§4 for coupling of N-L-alanyl-L-leucyl-primaquine with said protein.

The present invention also relates to medicinal compositions containing the new pharmaceutical forms according to this invention alone or in association with one or more compatible diluents or auxiliary agents. Said compositions may be administered by the parenteral route.

The compositions of the invention intended for parenteral administration may be aqueous or non aqueous sterile solutions, suspensions or emulsions. As solvent or carrier there may be used propyleneglycol, a polyethyleneglycol, vegetable oils more particularly olive oil or organic esters, for example ethyl oleate which are suitable for injection. Said compositions also may comprise wetting, emulsifying or dispersing agents. Sterilisation may be effected in several ways, for example by means of a bacteriological filter, by incorporating sterilising agents to the composition or by irradiation of said compositions. Said compositions also may be prepared in the form of solid sterile compositions which may be dissolved at the time of use into sterile water or any other injectable sterile medium.

The following Example illustrates a composition of the invention.

EXAMPLE OF COMPOSITION

In a conventional way, one prepares 100 cm³ of a sterile solution containing an amount of BSA-succinyl-L-ala-L-leu-L-ala-L-leuldaunorubicine which corresponds to 100 mg of free daunorubicine. This solution is administered by slow perfusion.

What we claim is:

1. A medicament compound of the formula

Carrier-spacer arm-Drug wherein
"drug" represents the therepeutically active principle containing a free amino function, said drug being selected from the group consisting of antitumoral anthracyclines, antimalarial and antileishmanial quinoleines,
"spacer arm" is a chain of peptidic nature represented by the sequence X—L—Leu wherein L—Leu represents a L—leucyl moiety bound through its carboxylic amino function to the amino function of the drug and X represents 1, 2 or 3 aminoacids which may be identical or different, selected from the group consisting of L-alanine, glycine and L—leucine and having a possible succinylated terminal amino function, and —"carrier" is a macromolecule of proteinic nature, the nature of which is related to the transport and/or affinity of action intended for the drug, said carrier being selected from the group consisting of bovine serum albumin, fetuine, immuno-globuline, asiafetuine or peptidic hormones.

2. The medicament according to claim 1, wherein the drug is selected from the group consisting of daunorubicine, doxorubicine and primaquine.

3. The medicament according to claim 1, wherein the spacer arm contains the sequence L-ala-L-leu, L-leu-L-ala-L-leu, L-ala-L-leu-L-ala-L-leu, (L-ala)₃-L-leu, gly-L-leu-gly-L-leu, L-ala-L-leu-gly-L-leu.

4. The medicament according to claim 1, wherein the peptidic hormone is selected from the group consisting of lactotropine or lactogenous placentary hormone.

5. The medicament according to claim 2, wherein the peptidic hormone is selected from the group consisting of lactotropine or lactogenous placentary hormone.

6. The medicament according to claim 3, wherein the peptidic hormone is selected from the group consisting of lactotropine or lactogenous placentary hormone.

7. A medicinal composition comprising the medicament according to claim 1, in a compatible pharmaceutically acceptable vehicle in effective concentrations for pharmacological application.

8. The medicament according to claim 1, wherein the "spacer arm" is selected from the group consisting of tri- and tetrapeptidic spacer arms.

9. The medicament according to claim 2, wherein the "spacer arm" is selected from the group consisting of tri- and tetrapeptidic spacer arms.

10. The medicament according to claim 8, wherein the "spacer arm" contains a sequence selected from the group consisting of L-leu-L-ala-L-leu; L-ala-L-leu-L-ala-L-leu; (L-ala)$_3$-L-leu; gly-L-leu-gly-L-leu; L-ala-L-leu-gly-L-leu.

11. The medicament according to claim 9, wherein the "spacer arm" contains a sequence selected from the group consisting of L-leu-L-ala-L-leu; L-ala-L-leu-L-ala-L-leu; (L-ala)$_3$-L-leu; gly-L-leu-gly-L-leu; L-ala-L-leu-gly-L-leu.

12. The medicament according to claim 8, wherein the "spacer arm" contains the sequence ala-leu-ala-leu.

13. The medicament according to claim 9, wherein the "spacer arm" contains the sequence ala-leu-ala-leu.

* * * * *

UNITED STATES PATENT OFFICE
CERTIFICATE OF CORRECTION

Patent No. 4,376,765                    Dated March 15, 1983

Inventor(s) Andre B. L. Trouet et al

It is certified that error appears in the above-identified patent and that said Letters Patent are hereby corrected as shown below:

Column 5, line 63 after "albumin" insert ---and 50 mg of 1-ethyl-3-(3-dimethylaminopropyl) carbodiimide---

Signed and Sealed this

*Twenty-first* Day of *August 1984*

[SEAL]

*Attest:*

*Attesting Officer*

GERALD J. MOSSINGHOFF

*Commissioner of Patents and Trademarks*